(12) United States Patent
Krüger et al.

(10) Patent No.: US 7,582,285 B2
(45) Date of Patent: Sep. 1, 2009

(54) COSMETIC PREPARATION CONTAINING A METALLIC PIGMENT

(75) Inventors: Peter Krüger, Schnaitach (DE); Hans-Jörg Kremitzi, Eckental (DE)

(73) Assignee: Eckart GmbH & Co. KG, Furth (DE)

( * ) Notice: Subject to any disclaimer, the term of this patent is extended or adjusted under 35 U.S.C. 154(b) by 0 days.

(21) Appl. No.: 10/588,226

(22) PCT Filed: Jan. 25, 2005

(86) PCT No.: PCT/EP2005/000682

§ 371 (c)(1), (2), (4) Date: Aug. 3, 2006

(87) PCT Pub. No.: WO2005/074865

PCT Pub. Date: Aug. 18, 2005

(65) Prior Publication Data

US 2007/0172438 A1    Jul. 26, 2007

(30) Foreign Application Priority Data

Feb. 3, 2004    (DE) .................. 10 2004 005 366

(51) Int. Cl.
- *A61K 8/18*     (2006.01)
- *A61Q 3/00*    (2006.01)
- *C09C 1/62*    (2006.01)
- *C04B 14/04*  (2006.01)

(52) U.S. Cl. .................. 424/61; 106/403; 106/404; 106/481; 427/217; 427/218; 428/403; 424/70.12; 424/59; 424/64; 424/62; 424/63; 424/401

(58) Field of Classification Search .............. 106/481, 106/404, 403; 427/217–218; 428/103, 403; 424/70.12, 401, 59, 61–64
See application file for complete search history.

(56) References Cited

U.S. PATENT DOCUMENTS

| | | | | |
|---|---|---|---|---|
| 4,894,224 A | * | 1/1990 | Kuwata et al. | 514/781 |
| 4,897,261 A | * | 1/1990 | Yamazaki et al. | 424/61 |
| 5,089,250 A | * | 2/1992 | Forestier et al. | 424/43 |
| 5,213,618 A | * | 5/1993 | Souma et al. | 106/403 |
| 5,261,955 A | * | 11/1993 | Nadkarni | 106/404 |
| 5,624,486 A | * | 4/1997 | Schmid et al. | 106/404 |
| 5,718,753 A | * | 2/1998 | Suzuki et al. | 106/403 |
| 5,733,364 A | * | 3/1998 | Schmid et al. | 106/403 |
| 5,931,996 A | * | 8/1999 | Reisser et al. | 106/404 |
| 6,398,861 B1 | | 6/2002 | Knox | |
| 2003/0051634 A1 | * | 3/2003 | Takahashi | 106/403 |
| 2003/0171479 A1 | * | 9/2003 | Lennon | 524/501 |
| 2004/0057918 A1 | * | 3/2004 | Chodorowski-Kimmes | 424/59 |
| 2006/0280712 A1 | * | 12/2006 | Kuroda et al. | 424/70.12 |

FOREIGN PATENT DOCUMENTS

| | | |
|---|---|---|
| DE | 44 37 753 A1 | 4/1996 |
| DE | 198 36 810 A1 | 2/2000 |
| DE | 101 14 445 A1 | 9/2002 |
| DE | 101 14 446 A1 | 9/2002 |
| EP | 0 673 980 A2 | 9/1995 |
| JP | 07-133211 A | 5/1995 |
| JP | 07-258025 A | 10/1995 |
| JP | 55004358 * | 1/1998 |
| JP | 2001-011342 | 1/2001 |
| JP | 2001-011342 A | 1/2001 |
| WO | WO 02/102333 A1 | 12/2002 |
| WO | WO 2004/026268 A2 | 4/2004 |

OTHER PUBLICATIONS

Ueda Tsutomu, "Pigment For Color Comestic", EP 07133211, Fuji Shikiso KK, May 23, 1995.
Mitani Hiroaki, "Pigment for Cosmetics", EP 07258025, Kira Keshohin KK, Oct. 9, 1995.

* cited by examiner

*Primary Examiner*—Michael A Marcheschi
*Assistant Examiner*—Pegah Parvini
(74) *Attorney, Agent, or Firm*—Browdy and Neimark, P.L.L.C.

(57) ABSTRACT

The invention relates to a cosmetic preparation containing a metallic effect pigment which consists of a metal substrate having a layer enclosing the substrate. Said layer is produced in a sol/gel method, has a barrier effect against sweat and saliva and prevents a direct contact between skin and metallic substrate, the metallic pigment being hydrophilic. The inventive preparation can be in the form of a cream, a lotion, an eye shadow, a nail varnish, a lipstick, a mascara, a gel, a make-up formulation or a self-tanning cream or lotion.

10 Claims, No Drawings

COSMETIC PREPARATION CONTAINING A METALLIC PIGMENT

The invention relates to a cosmetic preparation containing a metallic pigment. The cosmetic may be in the form of loose or pressed powders, eye shadows, lipsticks, eyeliners, nail polishes, blushes, hair colorants, mascaras, liquid self-tanners, and the like.

Cosmetics of the type in question, such as loose or pressed powders, eye shadows, lipsticks, eyeliners, nail polishes, blushes, hair colorants, mascaras, liquid self-tanners, and the like, are composed of a carrier material or a base formulation as well as color-imparting and effect-imparting means of various types, with the goal to obtain a certain color effect on the skin, lips or hair, or to optically cover up skin flaws.

These color-imparting and effect-imparting means may be colorants, lacquered organic colorants, inorganic or organic pigments and/or effect pigments, wherein especially in case of the effect pigments, special emphasis lies on the desire to attain a different color impression or brightness impression depending on the viewing angle of the applied preparation. To achieve this purpose, pearlescent pigments in particular have conventionally been used in the field of cosmetics.

Pearlescent pigments are based on flake-shaped mica particles as a substrate, which are coated with metal oxides, mainly with titanium dioxide or iron oxide. Pigments of this type on the basis of titanium oxide, however, are relatively transparent due to their composition and, as a rule, exhibit a color impression only at the so-called "glancing angle", whereas pigments that are based on iron oxide do provide more coverage, but the angle-dependent color impression or brightness impression is pushed to the background. The advantage of these pigments lies in their high degree of chemical and thermal stability, which in essence precludes negative effects for example on a binding agent, and in that they are well tolerated by the skin.

To the extent that metal effect pigments have been used for cosmetic purposes until now, they do have the advantage that they are covering, color-intensive and highly brilliant, however, they have the shortcoming, in particular, that they do not always meet the hygienic and application-specific requirements, considering especially that metal ions from the metal component, for example copper or zinc ions, are released into the carrier medium and can cause undesired effects, such as the gelling of binding agents and color changes. In the applied condition, contact with sweat or saliva may occur, which means with acidic or alkaline media, which can also cause an increased release of ions, which affect not only affect the carrier substance but may possibly lead directly to health-related damage, such as skin irritations.

From DE 44 37 753 A1 a lustrous pigment is known that is also usable for cosmetic purposes, which consists of at least five layers and is accordingly expensive to produce.

DE 198 36 810 A1 describes metal pigments that are coated in an aqueous medium, which involves the shortcomings that will be described below.

DE 101 14 445 A1 and DE 101 14 446 A1 describe iron pigments that are not approved for cosmetic applications. The same applies for the iron pigment according to EP 0 673 980 A2, which is treated at a raised temperature in an oxygen atmosphere.

U.S. Pat. No. 6,398,861 B1 describes a metal pigment composition, not a metal pigment as such. Reference is made to an aqueous system, and the use of tensides is mentioned, which are completely unsuitable for the inventive technical solution that will be described below.

With this as the starting point, the invention is based on the object to further develop a pigment of the above type in such a way that it better meets the hygienic, health-related and application-specific requirements than pigments that are conventionally used in the field of cosmetics.

This object is met according to the invention in such a way that a metallic substrate has a layer that uniformly encapsulates said metallic substrate, wherein said layer is produced in the sol-gel process, provides a barrier effect with respect to sweat and saliva, and prevents direct contact between the skin and metallic substrate.

In such a sol-gel process, a barrier layer is built up around the metallic substrate in organic solution or suspension from suitable monomeric metal-oxide pre-stages, e.g., alkoxy silanes, with the use of suitable catalysts. Compared to coating methods from aqueous solutions, e.g., with water glass, this process offers the advantage that no additional pretreatment is required to activate or degrease the base pigment, which is coated with auxiliary grinding agents, and the obtained layer cannot be contaminated through additional ions, such as e.g., chlorides or sulfates. Additionally, a layer that is obtained in this manner, since it was obtained from monomeric pre-stages, offers the advantage of a particularly even, dense and therefore high-quality, optically not perceptible layer, which is additionally also harmless from health-related and hygienic points of view, as they are relevant particularly for the cosmetic application.

A metal pigment that has been improved in this manner does not exhibit any, or only a significantly reduced, agglomeration tendency or flocculation tendency as compared to an uncoated metal pigment or one that has been coated in the aqueous system. The optical properties are not impacted by the surrounding layer, or only to a small degree. The same applies for the haptic properties.

The layer is preferably compatible with the binding agent/carrier material of a cosmetic preparation.

The layer preferably consists of $SiO_2$ that has been produced in sol-gel processes. Chemically similar surfaces are found in numerous cosmetic compositions, such as, e.g., in the form of bentonites.

For the present invention, it should be emphasized in particular that the metal pigment is water-wettable, so that it can be excellently and homogeneously incorporated into the widest variety of different cosmetic preparations.

The percentage of metal pigment in the formulation is advantageously 0.2% to 10%, especially 0.2% to 5%.

The preparation may be available especially in the form of a creme or lotion. In this context it is particularly advantageous that, with proper dosing, it imparts a uniform optical impression of the skin without changing the color of the skin. Provision may also be made, however, for the preparation to even out or cover up skin impurities.

The preparation may advantageously also be available in the form of a self-tanning creme or lotion.

In order to achieve that the preparation feels smooth in its application, it is necessary that the flake-shaped pigments have a large ratio of diameter to thickness (aspect ratio) and only minor surface roughness. This was achieved according to the invention in such a way that the silica particles that form the encapsulation have an average diameter of <100 nm. It is particularly advantageous if these particles are so fine that they exceed the limits of resolution even viewed under a scanning electron microscope.

Particularly favorable properties regarding optical appearance and stability can also be achieved in a cosmetic preparation that is implemented as a hair gel. An implementation as nail polish is possible as well.

The latter may be characterized in that it is based on nitrocellulose and may, among other things, also contain benzotriazoles, thus ensuring the shelf-life of metal-pigmented formulations also for extended periods of time.

The invention will be described in more detail below based on preferred example embodiments:

1st EXAMPLE EMBODIMENT

Blush (Hot Poured)

| INCI Name | Tradename | % w/w | Manufacturer |
|---|---|---|---|
| Phase 1 | | | |
| Silica | Speron P-1500 | 5 | Presperse |
| Mica | Azco Mica BC 1020 WG | 26 | Presperse |
| Red Iron Oxide | Cosmetic Russet C33-8075 | 5.9 | Sun Chemicals |
| Black Iron Oxide | Cosmetic Black C33-134 | 0.1 | Sun Chemicals |
| Copper (and) Silica | Visionaire Lava | 10 | Eckart |
| Phase 2 | | | |
| Isoseicosan | Permethyl 102A | 44 | Persperse |
| Carnauba Wax | Carnauba #1 Flake | 3 | Strahl & Pitsch |
| C12-C15 Alkyl Benzoate (and) Stearalkonium Bentonite (and) Propylene Carbonate | Tixogel FTN | 6 | Südchemie Rheologicals |

Method of Production:
1. The first four components of phase I are homogenized in a mixer until uniformly distributed.
2. Afterwards the pigment Visionaire Lava is added and mixed in homogeneously.
3. The components of phase 2 are stirred together in a mixer and heated to between 80° C. and 85° C.
4. The pigment mixture from phase 1 is slowly stirred into phase 2.
5. Mixing until homogenous.
6. At a temperature of 82° C., pouring into pan-like molds.

2nd EXAMPLE EMBODIMENT

Foundation (Water-In-Silicone)

| INCI Name | Tradename | % w/w | Manufacturer |
|---|---|---|---|
| Phase A | | | |
| Cyclopentasiloxane | Dow Corning 245 Fluid | 3 | Dow Corning |
| Cyclopentasiloxane (and) Dimethiconol | Dow Corning 1501 Fluid | 10 | Dow Corning |
| Titanium Dioxide (and) Methicone | BTD-M | 9.5 | Kobo |
| Mica (and) Methicone | GMS-MS2 | 3.68 | Kobo |
| Iron Oxides Yellow (and) Methicone | BXYO-MS2 | 1.45 | Kobo |
| Iron Oxides Red (and) Methicone | BXRO-MS2 | 0.78 | Kobo |
| Iron Oxides Black (and) Methicone | BXBO-MS2 | 0.2 | Kobo |
| Phase B | | | |
| Cyclopentasiloxane (and) PEG/PPG-18/18 Dimethicone | Dow Corning 5225C | 10 | Dow Corning |
| C30-45 Alkyl Methicone | Dow Corning Cosmetic Wax AMS C30 | 3 | Dow Corning |
| Cyclopentasiloxane | Dow Corning 245 | 2 | Dow Corning |
| Bronze powder (and) Silica | Visionaire Maize Gold | 2 | Eckart |
| Phase C | | | |
| Polysorbate 20 | Tween20 | 0.5 | Uniqema |
| Preservative | Uniphen P-23 | 0.3 | Induchem |
| Sodium Chloride | | 0.75 | |
| Deionized Water | | 52.84 | |

Method of Production:
1. Grind the pigments in phase A
2. Add the first three components of phase B to phase A and melt the phases together at 75° C.
3. Stir Visionaire Maize Gold into the combined phases A and B.
4. Mix together phase C and heat to 70° C.
5. Slowly add phase C to the mixture from phase A and B under homogenization.
6. Cool to room temperature in the paddle mixer.

3rd EXAMPLE EMBODIMENT

Metallic Styling Gel

| INCI Name | Tradename | % w/w | Manufacturer |
|---|---|---|---|
| Phase 1 | | | |
| Deionized Water | | 62.7 | |
| Acrylates/C10-30 Alkyl Acrylate Crosspolymer | Ultrez 21 | 0.66 | Noveon |
| Aminopropanol diluted 1:10 | AMP-95 | 1.33 | Angus |
| Phase 2 | | | |
| Propylene glycol | | 1 | |
| Phase 3 | | | |
| Polyquaternium-11 | Gafquat 755N | 4 | ISP |
| Deionized Water | | 25 | |
| Aminopropanol diluted 1:10 | AMP-95 | 0.02 | Angus |
| Phenoxyethanol (and) Methylparaben (and) Butylparaben (and) Ethylparaben (and) Propylparaben | Uniphen P-23 | 0.3 | Induchem |
| Mica (and) Titanium Dioxide | Prestige Dazzling Silver | 2.5 | Eckart |
| Aluminum (and) Silica | Visionaire Bright Silver Sea | 2.5 | Eckart |

Production:
1. Work the thickening agent into water.
2. Neutralize to a pH between 6.5 and 7 with AMP.
3. Mix into propylene glycol.
4. Mix in polyquaternium-11 in water to produce phase 3.
5. Neutralize phase 3 to a pH between 6.5 and 7.
6. Add phase 3 to the combined phases 1 and 2.
7. Mix in the preservative.
8. Mix in the pearlescent and metal pigments.

4th EXAMPLE EMBODIMENT

Moisturising Creme

| INCI Name | % w/w |
|---|---|
| Phase 1 | |
| Cyclomethicone | 72 |
| Dimethicone | 20 |
| C12-C15 Alkyl Benzoate (and) Stearalkonium Bentonite (and) Propylene Carbonate | 40 |
| Cetyl Dimethicone Copolyol | 4.8 |
| Visionaire Bright Natural Gold | 2 |
| Phase 2 | |
| Deonized Water | 252.5 |
| Sodium Chloride | 1.5 |
| Phenoxy ethanol (and) Methyl paraben (and) Butyl Paraben (and) Propyl paraben | 1.2 |

Production:
1. Mix and heat phase 1 to 78° C.
2. Mix and heat phase 2 to 78° C.
3. Add phase 2 to phase 1 under homogenization.
4. Cool to room temperature in the paddle mixer.

5th EXAMPLE EMBODIMENT

Bronze and Pearlescent Lipstick

| INCI Name | Tradename | % w/w | Manufacturer |
|---|---|---|---|
| Phase 1 | | | |
| Carnauba Wax | Carnauba #1 Flake | 3.0 | Strahl & Pitsch |
| Beeswax | Yellow Beeswax | 2.5 | Strahl & Pitsch |
| Candelilla Wax | SP-75 | 5 | Strahl & Pitsch |
| Ozokerite | Ozokerite 170 | 2 | Koster Keunen |
| PTFE | Microslip 519 | 2 | Micro Powders |
| Castor Oil | Castor Oil USP | 17.82 | SüdChemie Rheologicals |
| Polyisobutene | Permethyl 104A | 7 | Presperse |
| Isostearyl Isosterate | Isostearate d'Isostearyle | 5 | Gattefosse |
| Isononyl Isononanoate | Dermol 99 | 18 | Alzo |
| Caprylic/Capric Triglycerides | Liponate GC | 10 | Lipo |
| Phase 2 | | | |
| D&C Red #27 Aluminum Lake | 33% dispersion in Castor Oil | 10 | Sun Chemicals |
| FD&C Blue #1 Aluminum Lake | 50% Dispersion in Castor Oil | 0.03 | Sun Chemicals |

-continued

| INCI Name | Tradename | % w/w | Manufacturer |
|---|---|---|---|
| Phase 3 | | | |
| Propyl Paraben | | 0.10 | |
| BHT | | 0.05 | Eastman |
| Titanium dioxide (and) Mica (and) Iron Oxide | Prestige Bright Fire Red Pearl | 7.5 | Eckart |
| Bronze (and) Silica | Visionaire Bright Natural Gold | 7.5 | Eckart |
| Boron Nitride | Soft Touch CC5102 | 2.5 | Advanced Ceramics |

Production:
1. Mix phase 1 in a low-shear mixer.
2. Heat to between 80° C. and 84° C.
3. Add phase 2 and mix until homogenous.
4. Add phase 3
5. Pour into a lipstick mold at 70° C.

6th EMBODIMENT EXAMPLE

Bronze and Pearlescent Eye Shadow (Pressed)

| INCI Name | Tradename | % w/w | Manufacturer |
|---|---|---|---|
| Phase 1 | | | |
| Mica | Azco Mica BC 1020 wg | 34.9 | Presperse |
| Titanium Dioxide | Tronox CR-837 | 5.5 | Kerr McGee |
| Chromium Oxide Green | Chromium Oxide Green | 2.8 | LCW |
| Iron Oxide Yellow | Iron Oxide Yellow | 1.8 | Sun Chemical |
| Zinc Stearate | Zinc Stearate SAK 25 p | 5.5 | USP Blachford |
| Boron Nitride | Soft touch CCS 102 | 1.8 | Advanced Ceramic |
| Phase 2 | | | |
| Mica (and) Titanium Dioxide (and) Iron Oxide | Prestige Sparkling Lemon Gold | 18.35 | Eckart |
| Bronze (and) Silica | Visionaire Bright Natural Gold | 18.35 | Eckart |
| Phase 3 | | | |
| Dimethicone | Dow 200 | 5.5 | Dow Corning |
| Caprylic/Capric Triglycerides | Liponate GC | 5.5 | Lipo |

Production
1. Mix the components of phase 1 in a mixer until homogenous.
2. Add phase 2 and mix in homogeneously
3. Spray in phase 3 and mix in homogeneously

7th EMBODIMENT

Nail Polish

| Designation | % w/w | Manufacturer |
|---|---|---|
| ¼ second Parcell Ultra RS Nitrocellulose | 19.2 | Green Tree |
| ½ second Parcell Ultra RS Nitrocellulose | 2.7 | Green Tree |
| Ethyl Acetate | 32.1 | |
| n-Butyl Acetate | 27.6 | |
| Isopropyl Alcohol | 6.8 | |
| Dibutyl Phthalate | 4.2 | |
| Camphor | 1.4 | |
| Stearalkonium Bentonite | 1.0 | Süde Chemie Rheologicals |
| Visionaire ® Cinnamon | 5.0 | Eckart |

Production:
1. Disperse the stearalkonium bentonite in butyl acetate and activate with a mixture of 2:1 isopropanol/$H_2O$, with a percentage of 30 wt. % stearalkonium bentonite.
2. Add the solution to the remaining components, including any optionally desired additional colorants to attain special color combinations (except for Visionaire® Cinnamon), and blend uniformly.
3. Add Visionaire® Cinnamon under minimal shear stress and blend uniformly.

8th EXAMPLE EMBODIMENT

Silver Mascara

| Designation | % w/w |
|---|---|
| Phase A | |
| Deionized Water | 43.40 |
| Hydroxyethylcellulose | 0.30 |
| Triethanolamine | 1.50 |
| Phase B | |
| Visionaire Silver Sea | 10.00 |
| Spherical Silica Beads | 3.00 |
| Phase C | |
| Stearic Acid | 4.00 |
| GMS | 1.50 |
| PEG-100 Stearate | 1.00 |
| Beeswax | 5.00 |
| Carnauba wax | 3.00 |
| Candellila wax | 3.00 |
| Phase D | |
| Polyacrylic Emulsion | 5.00 |
| Phase E | |
| Phenoxylethanol | 1.00 |
| Methylparaben | 0.25 |
| Ethylparaben | 0.30 |
| Propylparaben | 0.15 |
| Butylparaben | 0.10 |

9th EXAMPLE EMBODIMENT

Self-Tanning Lotiion

| INCI Name/Designation | % w/w |
|---|---|
| Phase 1 | |
| Deionized Water | 55.625 |
| Sodium Chloride | 0.375 |
| Phase 2 | |
| C12-15 Alky Benzoate | 10.00 |
| Cyclomethicone | 8.00 |
| Dimethicone | 5.00 |
| Cylomethicone (and) Quaternium-18 Hectorite (and) Propylene Carbonate | 10.00 |
| Cetyl Dimethicone Copolyol | 1.20 |
| Phase 3 | |
| Visionaire Bright Natural Gold | 0.50 |
| Phase 4 | |
| Dihydroxyacetone | 4.00 |
| Deionized Water | 3.00 |
| Phase 5 | |
| Phenoxyethanol (and) Methylparaben (and) Butylparaben (and) Ethylparaben (and) Propylparaben | 0.30 |

Production:
1. Pour deionized water into a mixing vessel, dissolve sodium chloride in it while stirring, heat to 75° C.
2. Homogenize components of phase 2 and heat to 75° C.
3. Stir phase 3 into phase 2, keeping temperature at 75° C.
4. Add phase 1 to the mixture of phases 2 and 3 and disperse homogeneously.
5. Transfer the dispersion into a paddle mixer.
6. Slowly cool mixture to 50° C. while stirring
7. Add the premixed phase 4 as well as phase 5.
8. Cool to room temperature while stirring evenly.
9. Fill into suitable containers.

What is claimed is:

1. In a cosmetic preparation comprising a pigment and a carrier material or base formulation,
   the improvement wherein the pigment comprises
   a metal-effect pigment consisting of a metallic substrate and a single layer coating encapsulating the substrate, produced in a sol-gel process,
   said single layer providing a barrier effect with respect to sweat and saliva and preventing direct contact between the human body and the metallic substrate,
   said metal-effect pigment being water-wettable;
   wherein the single layer encapsulating the substrate consists essentially of $SiO_2$; and
   wherein silica particles generating the coating of the metal-effect pigment have an average diameter of <100 nm and the preparation feels accordingly smooth in its application.

2. A cosmetic preparation according to claim 1, in the form of a creme, a lotion, an eye shadow, a lipstick, a mascara, a gel, a make-up formulation, or a self-tanning creme or lotion.

3. A cosmetic preparation according to claim 1, wherein it imparts a uniform optical impression of the skin without changing the color of the skin.

4. A cosmetic preparation according to claim 1, wherein it evens out or covers up skin impurities.

5. A cosmetic preparation according to claims 1, wherein it contains a weight percentage of 0.2% to 40% of said metal-effect pigment.

6. A cosmetic preparation according to claim 1, wherein it is a nail polish.

7. A cosmetic preparation according to claim 6, wherein it is based on nitrocellulose.

8. A cosmetic preparation as in any of the preceding claims, wherein it additionally contains benzotriazoles.

9. The cosmetic preparation of claim 5 wherein said weight percentage of metal-effect pigment is 0.2 to 10%.

10. The cosmetic preparation of claim 5 wherein said weight percentage of metal-effect pigment is 0.2 to 5%.

* * * * *